US008257685B2

(12) United States Patent
Smyth et al.

(10) Patent No.: US 8,257,685 B2
(45) Date of Patent: Sep. 4, 2012

(54) SWELLABLE PARTICLES FOR DRUG DELIVERY

(75) Inventors: Hugh D. Smyth, Albuquerque, NM (US); Martin J. Donovan, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 1440 days.

(21) Appl. No.: 11/732,489

(22) Filed: Apr. 3, 2007

(65) Prior Publication Data
US 2008/0031824 A1 Feb. 7, 2008

Related U.S. Application Data

(60) Provisional application No. 60/788,942, filed on Apr. 4, 2006.

(51) Int. Cl.
*A61K 9/00* (2006.01)
*A61K 9/12* (2006.01)
*A61K 9/14* (2006.01)

(52) U.S. Cl. .......................................... 424/46; 424/489

(58) Field of Classification Search .................. 424/46, 424/489
See application file for complete search history.

(56) References Cited

U.S. PATENT DOCUMENTS

| 6,136,295 A | 10/2000 | Edwards et al. ................ 424/45 |
| 6,730,322 B1 | 5/2004 | Bernstein ...................... 424/486 |
| 2005/0112199 A1 | 5/2005 | Padval et al. |
| 2006/0052305 A1 | 3/2006 | Quay et al. |
| 2010/0272823 A1* | 10/2010 | Tarara et al. ................... 424/502 |

FOREIGN PATENT DOCUMENTS

| EP | 1579851 A2 | 9/2005 |
| EP | 1579851 A3 | 9/2005 |
| EP | 1642591 A1 | 4/2006 |
| WO | WO-9629998 A1 | 10/1996 |

OTHER PUBLICATIONS

Huheey, J. E. et al. Inorganic Chemistry, 4th Edition: Principles of Structure and Reactivity, HarperCollins: NewYork, 1993, pp. A-25.*
Heaf et al. ("In vitro assessment of combined antibiotic and mucolytic treatment for *Pseudomonas aeruginosa* infection in cystic fibrosis," Archives of Disease in Childhood, 1983, 58, pp. 824-836.*
"Hydrogen Element Facts" accessed on Feb. 27, 2011 at www.chemicool.com/elements/hydrogen.html.*
Chen et al. "Preparation of Cyclosporine A Nanoparticles by Evaporative Precipitation Into Aqueous Solution." International Journal of Pharmaceutics, vol. 242, pp. 3-14 (2002).
Chen et al. "Synthesis and Characterization of Superporous Hydrogel Composites." Journal of Controlled Release, vol. 65, pp. 73-82 (2000).
Cochrane et al. "Inhaled Corticosteriods for Asthma Therapy: Patient Compliance, Devices, and Inhalation Technique." Chest, vol. 117; pp. 542-550 (2000).
Elbert, et al. "Protein Delivery From Materials Formed by Self-Selective Conjugate Addition Reactions." Journal of Controlled Release, vol. 76, pp. 11-25 (2001).
Gonda "Aerosols for Delivery of Therapeutic and Diagnostic Agents to the Respiratory Tract." Critical Reviews in Therapeutic Drug Carrier Systems, vol. 6, Issue 4, pp. 273-313 (1990).
Hinds "Uniform Particle Motion." Aerosol Technology, pp. 42-74 (1999).
Kawaguchi et al. "Phagocytosis of Latex Particles by Leucocytes—I. Dependence of Phagocytosis on the Size and Surface Potential of Particles." Biomaterials, vol. 7, pp. 61-66 (1986).
Krenis et al. "Effect of Size and Concentration of Latex Particles on Respiration of Human Blood Leucocytes." Proc. Soc. Exp. Med., vol. 107, pp. 748-750 (1961).
Lansley "Mucociliary Clearance and Drug Delivery Via the Respiratory Tract." Advanced Drug Delivery Reviews, vol. 11, pp. 299-327 (1993).
Moren et al. "Aerosol Dosage, Forms and Formulations." Aerosols in Medicine. Principles, Diagnosis and Therapy, Ch. 10, pp. 261-287 (1985).
Patton et al. Inhaled Insulin. Advanced Drug Delivery Reviews, vol. 35, pp. 235-247 (1999).
Peppas et al. "Physiochemical Foundations and Structural Design of Hydrogels in Medicine and Biology." Annu. Rev. Biomed. Eng., vol. 2, pp. 9-29 (2000).
Rudt et al. "In Vitro Phagocytosis Assay of Nano- and Microparticles by Chemiluminescence. I. Effect of Analytical Parameters, Particle Size and Particle Concentration." Journal of Controlled Release, vol. 22, pp. 263-272 (1992).
Smyth et al. "Carriers in Drug Powder Delivery—Implications for Inhalation System Design." Am. J. Drug Deliv., vol. 3(2), pp. 117-132 (2005).
"European Application Serial No. 07754563.0, Extended Search Report mailed Dec. 29, 2011", 7 pgs.
Bowen, P ,"Particle Size Distribution Measurerment from Millimeters to Nanometers and from Rods to Platelets", Journal of Dispersion Science and Technology, 23(5), 33 pgs, 2002.
"Australian Application Serial No. 2007240986, Office Action mailed Nov. 11, 2011", 2 pgs.

* cited by examiner

*Primary Examiner* — James H. Alstrum-Acevedo
(74) *Attorney, Agent, or Firm* — Schwegman Lundberg & Woessner, P.A.

(57) ABSTRACT

Swellable particles for delivery of a drug or other working agent to the pulmonary system are provided. The swellable particles include a dehydrated (dry) aerodynamic particle diameter of 5 µm or less to enable delivery to the respiratory tract, such as for example to the tracheo-bronchial airways of the upper respiratory tract and/or to the alveolic regions of the deep lung, and a hydrated particle diameter that is greater than 6 µm volume mean diameter to retard or prevent their phagocytosis by the macrophages present in airways of the respiratory tract.

18 Claims, No Drawings

SWELLABLE PARTICLES FOR DRUG DELIVERY

This application claims priority and benefits of provisional application Ser. No. 60/788,942 filed Apr. 4, 2006, the entire disclosure of which is incorporated herein by reference.

BACKGROUND OF THE INVENTION

The present invention relates generally to swellable biodegradable particles for use in delivering a therapeutic or other agent to the pulmonary system and, more particularly, to swellable biodegradable particles that have dehydrated sizes for delivery to the pulmonary system and that swell on hydration in the pulmonary tract to larger sizes to achieve controlled release of a drug or other agent from the particle structure.

BACKGROUND OF THE INVENTION

Delivery of therapeutic agents to the pulmonary system has been used for the treatment of local lung diseases such as asthma, cystic fibrosis, and chronic obstructive pulmonary disease (A. J. Hickey, editor, Inhalation Aerosols: Physical and Biological Basis for Therapy, New York: Marcel Dekker, Inc. 1996). Relative to systemic oral or injection drug delivery, local delivery of respiratory drugs to the lungs provides advantages because it: (1) requires smaller doses of the drug; and (2) minimizes systemic toxicity by allowing delivery directly to the site of the disease. Delivery of systemically acting agents has also been investigated, such as for the administration of proteins and peptides (e.g. insulin) as described by Patton et al., in "Inhaled insulin", Adv. Drug. Deliv. Rev. 35, pp. 235-247 (1999).

However, pulmonary delivery of drugs is limited by several major issues including poor efficiency of deposition in the respiratory tract and excessive removal of the drug by the oropharyngeal cavity, poor control over the site of deposition of the drug within the respiratory tract, poor reproducibility of dosing due to the dependence on breathing patterns of the patient, and too rapid clearance and/or absorption of the drug from the pulmonary system potentially resulting in inappropriate drug concentrations at the target site and even toxic effects.

A controlled release delivery system for drugs delivered locally to the lung would provide a very desirable method to effectively treat respiratory and systemic diseases. Moreover, controlled release of respiratory drugs may offer significant clinical benefit to millions of patients with respiratory disease by allowing them to take treatments for such diseases as asthma less frequently and to receive more prolonged and controlled relief. Controlled delivery of drugs to the lung also offers the potential for improved safety by moderating the drug peaks and troughs of immediate release drugs, which can cause added toxicity or reduced efficacy. Also, controlling the release of two or more therapeutic agents from a single particle system delivered to the pulmonary system would have significant benefits for co-localization of the agents within the respiratory tract. The likelihood of synergism or additive effects between agents would be significantly increased.

Currently available pulmonary delivery systems are not ideal, delivering inaccurate doses, requiring frequent dosing and losing significant amounts of drug in the delivery process. Most asthma drugs delivered via inhalation are immediate-release formulations that must be inhaled multiple times per day (Cochrane et al. Inhaled Corticosteroids for Asthma Therapy: Patient Compliance, Devices, and Inhalation Technique Chest. 117, pp. 542-550, 2000). This frequent inhalation tends to discourage patient compliance. When patients forget to take their medicine they may experience complications which may result in increased emergency room visits and hospitalizations. In a recent analysis of published studies of patient compliance with asthma medications, patients took the recommended doses of medication on only 20 to 73% of days (Cochrane et al. Inhaled Corticosteroids for Asthma Therapy: Patient Compliance, Devices, and Inhalation Technique, Chest. 117, pp. 542-550, 2000). The percentage of under-use days ranged from 24 to 69%. In addition, immediate release formulations often deliver drug levels that peak and trough, causing undesirable toxicity or inadequate efficacy.

Although promising, inhaled formulations face difficult challenges in maintaining effective drug concentration in the lungs for extended periods. Factors contributing to the short duration of drug action following pulmonary delivery include: (1) the rapid mucociliary clearance rates (approximately 1.7-4.9 mm/min) resulting in a very short half-life for inhaled particles (approximately 0.5-2 hr) (Lansley, A. B., 1993. Mucociliary clearance and drug delivery via the respiratory tract. Adv Drug Del Rev. 11, 299-327); (2) phagocytosis of particles by the alveolar macrophages; and; (3) rapid absorption of drug molecules (Mw<1000 Da) to the systemic circulation with a mean half-time for absorption of <2 hr.

The pulmonary region has several particle clearance mechanisms. The relative importance of each clearance mechanism varies depending on the physicochemical properties of the particle. Particle retention in the pulmonary region is longer than that of the ciliated airways. After deposition, uptake of particles by alveolar macrophages is very rapid. An initial fast phase of clearance is related to phagocytosis by alveolar macrophages.

There are limited technologies available to circumvent the natural clearance mechanisms of the airways that largely prevent sustained release particles from being effective. A number of prior art references, including, but not limited to U.S. Pat. Nos. 6,136,295 to Edward, et al.; and 6,730,322 to Bernstein, et al., describe particles that have been designed to have low densities (large porous particles). Although geometrically large, those particles are aerodynamically much smaller.

Generally to achieve sustained release, particles must be delivered to the airways and avoid mucociliary clearance, uptake by alveolar macrophages, and prevention of rapid absorption from the lung. Avoiding mucociliary clearance can be achieved by avoiding particle deposition in the tracheobronchial region where ciliated epithelia are present. Generally an aerodynamic particle size must be less than around 5 μm to accomplish this. Once particles are deposited in the peripheral airways where the mucociliary clearance mechanism is not present, particles must avoid alveolar macrophage uptake that can rapidly clear therapeutic compounds. Avoidance of macrophages can be accomplished by (1) creating particles that are not recognizable as foreign particulates (stealth particles); (2) providing particles that are physically too large to be engulfed by macrophages or which delay engulfment; or (3) providing particles that are too small to be recognized by macrophages (nanoparticles).

Current sustained release pulmonary systems as described by the cited prior art generally comprise large porous particle technologies. The main problems with these systems is the low drug loading possible in the particle matrix, the special physicochemical properties of the drug required for inclusion in these particle systems, and the limits on how long drug may be sustained. The present invention overcomes these problems by using swelling particles to improve sustained release. The swelling particles of the present invention include the drug or other working agent being delivered on and/or in a biocompatible and biodegradable swellable matrix that preferably enables deep lung delivery and avoids clearance by the alveolar macrophages. In addition, the matrix materials can be modified to modulate the drug release characteristics or to improve compatibility of the drug with the matrix system.

SUMMARY OF THE INVENTION

The present invention provides improved swellable particles for delivery to the pulmonary system, and to a method for their incorporation and administration of a working agent, such as including but not limited to a therapeutic agent, diagnostic agent, prophylactic agent or imaging agent. The swellable particles include dehydrated (dry) aerodynamic particle diameters to enable delivery to the respiratory tract, such as for example to the tracheo-bronchial airways of the upper respiratory tract and/or to the alveolar regions of the deep lung, and hydrated particle diameters that are greater than 6 μm volume mean diameter to retard or prevent their phagocytosis by the macrophages present in airways of the respiratory tract.

In an illustrative embodiment of the invention, the dehydrated (dry) particles are made of a biodegradable material, have a mass median aerodynamic particle diameter between 0.5 μm and 5 μm, and are capable of swelling to a hydrated geometric particle diameter greater than 6 μm volume mean diameter. In a preferred embodiment of the invention, at least 90%, more preferably 95% to 99%, of the particles have an aerodynamic particle diameter not exceeding 5 μm and swell to a size of greater than 6 μm volume mean diameter. The particles may be formed of biodegradable materials such as including, but not limited to, a biodegradable natural or synthetic polymer, a protein, a carbohydrate, or combinations thereof. For example, the particles may be formed of a multi-branched polyethylene glycol (PEG) hydrogel polymer. Other examples include particles formed of biodegradable polymers such as dextrans, hydroxyethylmethylacrylate, or other biocompatible and biodegradable swellable polymeric systems. The swellable particles can be used for enhanced delivery of one or more working agents to the airways of the respiratory tract, including to the alveolar region of the lung. The particles incorporating one or more working agents may be effectively aerosolized for administration to the respiratory tract to permit systemic or local delivery of a wide variety of therapeutic and other agents. They optionally may be co-delivered with larger carrier particles (not carrying a therapeutic or other agent) which have for example a mean diameter ranging between about 50 μm and 150 μm.

The present invention is advantageous in that the dehydrated (dry) particles possess an aerodynamic diameter such that a) they are able to reach one or more target regions of the respiratory tract, including the tracheo-bronchial airways of the upper respiratory tract and/or to the alveolar regions of the deep lung, b) they can deliver a payload of one or more working agents without premature release, c) they are swellable by hydration in the airways to a size that retards or prevents their uptake and removal by macrophages, and d) they can provide controlled release of the working agent(s) at predictable rates following hydration.

Other features and advantages of the present invention will become apparent from the following detailed description.

DETAILED DESCRIPTION OF THE INVENTION

The present invention provides swellable, biodegradable particles for improved delivery of therapeutic and other working agents to the respiratory tract. The working agents which can be delivered via the particles include, but are not limited to, a therapeutic agent, diagnostic agent, prophylactic agent, imaging agent, or combinations thereof.

In an illustrative embodiment of the invention, the swellable particles initially comprise dehydrated (dry) powder particles having mass median aerodynamic particle diameter of 5 μm or less to enable delivery to the respiratory tract, such as for example to the tracheo-bronchial airways of the upper respiratory tract and/or to the alveolic regions of the deep lung, and having hydrated particle diameter that is greater than 6 μm volume mean diameter to retard or prevent their phagocytosis by the macrophages present in airways of the respiratory tract. The dehydrated (dry) particles typically have a mass median aerodynamic diameter between 0.5 μm and 5 μm, and typically are capable of swelling to a hydrated geometric diameter greater than 6 μm to 50 μm volume mean diameter. At least 90%, more preferably 90% to 95%, of the particles have an aerodynamic diameter of 5 μm or less and swell to a size of greater than 6 μm volume mean diameter.

The mass median aerodynamic diameter (MMAD) is typically obtained from conventional aerosol sizing instruments, such as cascade impactors and/or time of flight instruments such as the TSI Aerodynamic Particle Sizer (TSI Incorporated, Shoreview, Minn.). This size determination occurs where 50% of the mass of the particles, when classified by their aerodynamic size, are below this diameter (i.e. the MMAD). That is, 50% of the mass of particles have a diameter lower than the MMAD and 50% of the mass of particles have a diameter higher than the MMAD. This measure of particle size converts the particle in question (which can have different densities, shapes, surface and aerodynamic drag) into a sphere having a density equal to 1 and provides an equivalent sphere diameter, even though the particle may have a flake, acicular or other non-spherical shape. For example, the aerodynamic diameter is defined as the diameter of the spherical particle with a density of 1 g/cm$^3$ (the density of a water droplet) that has the same settling velocity as the particle and is given by the following equation (see Hinds, W. I., "Uniform Particle Motion," in *Aerosol Technology* 1999, pp. 42-74, John Wiley and Sons Inc.): $d_a = d_p(\rho_p)^{1/2}$ where $d_p$ is the diameter of the particle and $\rho_p$ is its density in g/cm$^3$. The aerodynamic diameter may be thought of as the diameter of a spherical droplet of water possessing the same aerodynamic properties as the particle. For example, if a particle has an aerodynamic diameter of 1 μm, it acts aerodynamically identical to a 1 μm water droplet regardless of the particle's actual size, shape, or density. By adjusting the mean diameter and density of an aerosol population, the particles can be tailored to possess the exact aerodynamic diameter necessary for delivery to a specified lung region. The diameters of the swellable particles in a sample can range depending upon on factors such as particle composition and methods of synthesis. The distribution of size of particles in a sample can be selected to permit optimal deposition within targeted sites within the respiratory tract.

The equivalent sphere diameter allows one to directly compare particles with different particle geometries and compare them only on the basis of aerodynamics, which is the functional size characteristic of importance for delivery of the particles to the respiratory tract. The MMAD is selected to describe the dehydrated (dry) particles because it is useful in predicting the deposition of dry powder particles within the airways.

The volume mean diameter is used to describe the hydrated particles because the particles will have swollen in size after hydration in the airways. The volume mean diameter will increase from the dry state to the hydrated state regardless of the particle shape. The volume mean diameter is also an equivalent sphere diameter whereby the particle in question is converted to a sphere of equivalent volume, even though the particle may have a flake, acicular or other non-spherical shape. In terms of functionality, the volume of the particle is important because it is related to how well the macrophage cells in the airways can clear the particles; i.e. their volume is important for retarding or avoiding the clearance mechanisms of the respiratory tract. The volume mean diameter can be determined by testing as follows: using hydrogel particles dispersed in buffer solution, a laser light scattering instrument can be used to measure volume diameter changes in the particle geometry upon hydration. A low energy liquid dispersion attachment may also be used to minimize particle aggregation. Alternatively, particle swelling can be quantified via confocal microscopy.

The swellable particles may be formed from any biodegradable, and preferably biocompatible polymer, copolymer, or blend, which is capable of forming particles with a mass median aerodynamic diameter between 0.5 and 5 µm, but can also swell to a geometric diameter of greater than 6 µm volume mean diameter. For purposes of illustration and not limitation, the particles can be formed of a swellable biodegradable natural polymer, synthetic polymer, protein, carbohydrate, or combinations thereof. For example, the particles may be formed of a multi-branched polyethylene glycol (PEG) hydrogel polymer. Other examples include particles formed of biodegradable polymers such as dextrans, hydroxyethylmethylacrylate, or other biocompatible and biodegradable swellable polymeric systems.

For purposes of further illustration and not limitation, the swellable particles also can be made from bulk eroding hydrogel polymers, such as those based on polyesters including poly(hydroxy acids) can be used in practice of the invention. Moreover, surface eroding polymers such as polyanhydrides may be used to form the swelling particles. For example, polyanhydrides such as poly[(p-carboxyphenoxy)-hexane anhydride] (PCPH) may be used. For example, polyglycolic acid (PGA) or polylactic acid (PLA) or copolymers thereof may be used to form the swellable particles, wherein the polyester has incorporated therein a charged or functionalizable group such as an amino acid as described below. Other polymers include polyamides, polycarbonates, polyalkylenes such as polyethylene, polypropylene, poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof which are capable of forming swellable particles described above. Polymers may be selected with or be modified to have the appropriate stability and degradation rates in vivo for different controlled drug delivery applications.

Features of the swellable particle which can contribute to swelling include degree of polymer cross-linking, monomer size, and porosity. A rough particle surface texture also can reduce particle agglomeration and provide a highly flowable powder, which is ideal for aerosolization via dry powder inhaler devices, leading to lower deposition in the mouth, throat and inhaler device. Moreover, administration of the swellable particles to the lung by aerosolization permits deep lung delivery of therapeutic aerosols where the particles can swell after hydration on the airway surfaces). In order to serve as efficient drug carriers in drug delivery systems, the swellable particles preferably are biodegradable and biocompatible, and optionally are capable of biodegrading at a controlled rate for delivery of a drug.

In an illustrative embodiment of the invention, biodegradable and/or biocompatible hydrogel particles are formed from acrylated 8-arm PEG (20 kDa) crosslinked with dithiothreitol, as described by Hubbel et al. *Journal of Controlled Release* 76:11-25 (2001), the teachings of which are incorporated herein by reference. Alternate methods of crosslinking the acrylated polymers include photopolymerization, other covalent crosslinking methods (polycysteine), ionic crosslinking, and physical crosslinking (entanglements between highly branched and high molecular weight polymers).

In the synthesis, both the molecular weight, degree of branching (e.g. 8-arm to 4-arm), and the concentrations of the reactants may be altered to change the pore size of the hydrogels, and thereby adjust the release rate of the therapeutic within the polymer matrix.

Alternatively, the biocompatible hydrogel particles may be formed of multiple polymer molecules, copolymeric hydrogels, chosen to grant specific and advantageous characteristics to the system. In one preferred embodiment, hydrogels are constructed from a block copolymer configuration of repeating units of poly-lactic acid (PLA) and polyethylene glycol. The PLA confers rapidly hydrolyzable ester bonds, whereas the PEG backbone prevents both the rapid degradation of the polymer and adsorption of proteins to the hydrogel surface and subsequent removal by the immune system.

The swellable particles can be made using a variety of particle-forming processes and in a variety of particle shapes. For example, swelling polymeric particles can be prepared using spray drying, solvent evaporation, polymer micronization, and other methods well known to those of ordinary skill in the art. Swellable particles comprising hydrogels can be synthesized during emulsification with an aqueous phase with a non-aqueous phase to form microspheres of hydrogel that can be modulated in size by changing parameters of the emulsion (e.g. non-aqueous phase composition, concentration of reactants, mixing speed and shear introduced into the emulsion, presence of surfactants and surfactant types, etc). Swellable particles comprising hydrogels also can be synthesized during spraying so that the hydrogel particles form and are cross linked while dispersed as a droplet. Alternately, disks, spheres, cubes, irregular shapes, thin films of hydrogels can be synthesized and then broken into (comminuted) small respirable, swellable particles using milling and micronization methods. The comminuted particles can have a flake, acicular or other non-spherical shape.

For example, the dried hydrogels made can be broken down into macroparticles using a rotary blade mill (M 20 Universal mill, IKA® Werke GmbH, Germany). Size reduction to narrowly dispersed micron size particles suitable for inhalation can then be performed using a fluid energy mill that uses impinging air jets to finely micronize the material. Particle size of the resultant material is controlled by the parameters of fluid energy milling (air pressures) and can also be separated using an air classifier. Particle size can be determined using a Sympatec Helos laser diffraction instrument and also conventional cascade impaction techniques. Milled particles exhibit much faster rates of swelling than unmilled particles as a result of the increased surface area available for water uptake.

The swellable particles may be fabricated or separated, for example by sieving or air separation methods, to provide a particle sample with a preselected size distribution to provide the desired MMAD in the dry powder state. As mentioned above, the selected range within which a certain percentage of the particles must fall preferably is controlled such that at least 90%, or even more preferably 95% or 99%, have an aerodynamic particle diameter between 0.5 μm and 5 μm.

A particular process for making swellable particle starts with hydrated films or hydrogel masses, which can then be processed for particle size reduction and micronization. For example, the hydrated films or hydrogel masses can be extruded through a fine orifice or mesh to reduce particle size. The particles can then be dehydrated. Alternatively, particles can be produced after dehydration of the hydrogel films. Dehydration is achieved using methods such as a vacuum oven drying, lyophilization, solvent displacement by volatiles, among others. The dried hydrogels can be broken down into particles using a rotary blade mill (M 20 Universal mill, IKA® Werke GmbH, Germany). Size reduction to narrowly dispersed micron size particles suitable for inhalation can then be performed using a fluid energy mill that uses impinging air jets to finely micronize the material.

The swellable particles can be used for enhanced delivery of one or more working agents to the airways of the respiratory tract, including the alveolar region of the lung. The particles incorporating one or multiple working agents may be effectively aerosolized for administration to the respiratory tract to permit systemic or local delivery of a wide variety of therapeutic agents. For example, particle size of an inhaled aerosol is the primary determinant of the deposition pattern within the airways. They optionally may be co-delivered with larger carrier particles (i.e. not carrying a working agent) which have for example a mean diameter ranging between about 50 μm and 150 μm.

Incorporation of a therapeutic or other working agent within the particle can be accomplished using a variety of methods. For example, inclusion/incorporation of a working agent inside the particles comprising hydrogels described herein can be achieved by entrapping the working agent in the hydrogel polymer network so as to control the release of the drug (or other working agent) from the particle at specifically desired rates. Entrapment can be achieved by performing the cross linking of the polymers in the presence of the working agent (e.g. drug) such that the working agent (e.g. drug) is entrapped within the polymer network that forms the hydrogel network. Entrapment also can be achieved by performing the cross linking of the polymers prior to placing the hydrogels in the presence of the working agent (e.g. drug) such that the working agent is entrapped within the polymer network by diffusing into the hydrogel. Moreover, multiple working agents (e.g. drugs) can be loaded into the same swellable particles using the same or different methods since beneficial release rates may be achieved by loading differently or using the same methods.

The therapeutic agent (or other working agent) to be loaded into the swellable hydrogel particles can take various forms including a drug in solution such that the drug is a molecular dispersion throughout the hydrogel particle, a drug in suspension, a colloidal dispersion, a nanoparticle system dispersed throughout the hydrogel particle, or a drug in liposomes, lipid dispersions, nanocapsules, polymeric nanoparticles, etc dispersed throughout the hydrogel particle.

For purposes of further illustration and not limitation, incorporation of a therapeutic agent (or other working agent) within the particle can be accomplished by the following methods:

a) Encapsulation of the therapeutic agent within a nanoparticle and placement of the nanoparticle within the particle. For example, Ibuprofen can be encapsulated within Lecithin (phophotidylcholine) nanoparticles 200-400 nm in diameter. These nanoparticles were prepared using the method of Chen et al, 2002 (Chen, X., Young, T. J., Sarkari, M., Williams, R. O., Johnston, K. P., Preparation of cyclosporine A nanoparticles by evaporative precipitation into aqueous solution, International Journal of Pharmaceutics 242, (2002) 3-14). The nanoparticles are incorporated into the swellable particles by physical entrapment in the hydrogel network by performing crosslinking reactions in the presence of the nanoparticles in the reactant solution of the 20 kDa 8-arm acrylated PEG with dithiothreitol as described below for the illustrative embodiment. Nanoparticles can be designed to have differential rates of release from the swellable particles based on their relative sizes, hydrophilic nature, ionic properties, and diffusion coefficients.

b) Direct encapsulation of the molecule within the matrix of the polymer network (e.g. PEG hydrogel network) of the swellable particle. For example, Rhodamine therapeutic agent can be trapped within the polymer network (PEG hydrogel network) during the crosslinking of the 20 kDa 8-arm acrylated PEG with dithiothreitol as described below for the illustrative embodiment.

c) Attachment of the therapeutic agent to the polymer network itself (PEG hydrogel network) through chemical interactions (covalent, ionic, and hydrogen bonds). For example, N-acetylcysteine mucolytic agent can be attached to the polymer network of 8-arm acrylated PEG crosslinked with dithiothreitol through covalent bonds between the thiol group on the N-acetylcysteine and one thiol group on the dithiothreitol with the other thiol group of dithiothreitol bonded to an acrylate group of the polymer network. The N-acetylcysteine mucolytic agent can be reversibly covalently bound to the hydrogel network of the particle such that the N-acetylcysteine functions to decrease the viscosity of the mucus by disrupting the disulfide bonds formed between adjacent cysteine residues. This disruption of mucus disulfide bonds is readily achieved since the disulfide bonds are transferred between cysteine residues. This facilitates prolonged and localized mucolytic release around the hydrogel particle structure, increasing transport rates through the CF mucus environment.

Using these encapsulation methods, numerous therapeutic and other working agents, ranging from small and hydrophilic to large and hydrophobic, may be incorporated into the swellable particles for the aerosolized treatment of cystic fibrosis, lung cancer, asthma, chronic obstructive pulmonary disease (COPD), acute bronchitis, emphysema, tuberculosis, or systemic diseases. For example, loading of Rhodamine therapeutic agent in PEG hydrogel particles described herein has been achieved during polymerization or after the particles were made. High loading of this drug was obtained using both methods. For example, approximately 35% w/w Rhodamine therapeutic agent was present after washing surface drug from the hydrogel particles.

Any of a variety of therapeutic treating agents, prophylactic agents, diagnostic agents, imaging agents such as radioisotopes, or other active working agents can be incorporated within the swellable particles. The swellable particles can be used to locally or systemically deliver a variety of therapeutic agents to the respiratory tract. Examples of working agents include synthetic inorganic and organic compounds, proteins and peptides, polysaccharides and other sugars, lipids, and nucleic acid sequences having therapeutic, prophylactic, diagnostic or imaging activities. Nucleic acid sequences include genes, antisense molecules which bind to complementary DNA to inhibit transcription, and ribozymes. The working agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. In some instances, the proteins may be antibodies or antigens which otherwise would have to be administered by injection to elicit an appropriate response. Compounds with a wide range of molecular weight can be encapsulated, for example, between 100 and 500,000 grams per mole.

Proteins are defined as comprising 100 amino acid residues or more; peptides are less than 100 amino acid residues. Unless otherwise stated, the term protein refers to both proteins and peptides. Examples include insulin and other hormones. Polysaccharides, such as heparin, can also be administered.

The swellable polymeric aerosols are useful as carriers for a variety of inhalation therapies. They can be used to encapsulate small and large drugs, release encapsulated drugs over time periods ranging from hours to months, and withstand extreme conditions during aerosolization or following deposition in the lungs that might otherwise harm the encapsulated therapeutic.

For example, the swellable particles may include a therapeutic agent for local delivery within the lung, such as agents for the treatment of asthma, emphysema, or cystic fibrosis, or for systemic treatment. For example, genes for the treatment of diseases such as cystic fibrosis can be administered, as can beta agonists for asthma. Other specific therapeutic agents include, but are not limited to, insulin, calcitonin, leuprolide (or LHRH), G-CSF, parathyroid hormone-related peptide, somatostatin, testosterone, progesterone, estradiol, nicotine, fentanyl, norethisterone, clonidine, scopolamine, salicylate, cromolyn sodium, salmeterol, formoterol, albuterol, and valium.

The particles including a therapeutic agent may be administered alone or in any appropriate pharmaceutical carrier, such as an inert sugar particle system typically used in a powder inhaler, for administration to the respiratory system. They can be co-delivered with larger carrier particles (not including a therapeutic agent) possessing mass mean diameters for example in the range 50 μm to 150 μm.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6:273-313, 1990; and in Moren, "Aerosol dosage, forms and formulations," in: Aerosols in Medicine. Principles, Diagnosis and Therapy, Moren, et al., Eds, Elsevier, Amsterdam, 1985, the disclosures of which are incorporated herein by reference.

The relatively large size of swollen aerosol particles deposited in the deep lungs minimizes potential drug losses caused by particle phagocytosis. The swellable polymeric matrix also facilitates as a therapeutic carrier to provide the benefits of biodegradable polymers for controlled release in the lungs and long-time local action or systemic bioavailability. Denaturation of macromolecular drugs can be minimized during aerosolization since macromolecules are contained and protected within a polymeric matrix shell. Coencapsulation of peptides with peptidase-inhibitors can minimize peptide enzymatic degradation.

For purposes of still further illustration and not limitation, the swellable particles can include a working agent that comprises a mucolytic agent alone or together with another working agent such as antibiotic agent, a cytotoxic agent, other mucolytic agents, an RNA interfering agent which includes siRNA and miRNA, a gene, or combinations thereof. The working agent also can comprise multiple cytotoxic agents, a cytotoxic agent and an RNA interfering agent, or other combinations of working agents for purposes of further illustration.

In comparison to non-swellable particles, the swellable particles pursuant to the present invention also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond 3 μm Kawaguchi, H. et al., Biomaterials 7: 61-66 (1986); Krenis, L. J. and Strauss, B., Proc. Soc. Exp. Med., 107:748-750 (1961); and Rudt, S, and Muller, R. H., J. Contr. Rel., 22: 263-272 (1992). For particles of statistically isotropic shape (on average, particles of the powder possess no distinguishable orientation), such as spheres with rough surfaces, the particle envelope volume is approximately equivalent to the volume of cytosolic space required within a macrophage for complete particle phagocytosis.

Swellable particles thus are capable of a longer term release of a therapeutic or other working agent. Following inhalation, swellable biodegradable particles can deposit in the lungs (due to their relatively small size), and subsequently undergo swelling, slow degradation and drug release, without the majority of the particles being phagocytosed by alveolar macrophages. A drug can be delivered relatively slowly into the alveolar fluid, and at a controlled rate into the blood stream, minimizing possible toxic responses of exposed cells to an excessively high concentration of the drug. The swellable particles thus are highly suitable for inhalation therapies, particularly in controlled release applications. The preferred mass median aerodynamic diameter for swellable particles for inhalation therapy is between 0.5 to 5 μm (prior to swelling). After swelling, the particles have geometric sizes of greater than 6 μm volume mean diameter in the airways.

The particles may be fabricated with the appropriate material, surface roughness, diameter, density, and swelling properties for localized delivery to selected regions of the respiratory tract such as the deep lung or upper airways. For example, larger particles or more dense particles may be used for upper airway delivery, or a mixture of different sized particles in a sample, provided with the same or different therapeutic agent may be administered to target different regions of the lung in one administration.

The swellable particles can be delivered by inhalation methods using propellant driven metered dose inhalers wherein hydrofluroalkane and/or alkane liquefied gas propellants are used in these formulations with other excipients included for stabilization of the preparations. Dry powder inhalers can use swellable hydrogel particles prepared for aerosolization and inhalation. Use of a dry powder inhaler may require blending with so called "carrier" particles (See Smyth and Hickey, Carriers in Drug Powder Delivery: Implications for Inhalation System Design, American Journal of Drug Delivery, Volume 3, Number 2, 2005, pp. 117-132). These carrier particles are typically lactose, sucrose, glucose or other particles that are blended with the swellable particles for aerosolization. Typically, the carrier particles are sized between 50-500 μm as determined by sieve analysis and make up from 90-99% w/w of the powder placed in the inhaler for aerosol dispersion and inhalation. Dry powder insufflation, liquid spray systems, and nebulizers also can be used to deliver the swellable particles.

Moreover, modulation of the aerodynamic particle size of the aerosol particles can be used to target different regions of the airways. Attachment of targeting ligands on the surface of the swellable particles can result in their localization at specific sites within the respiratory systems, such as for lung cancer a targeting ligand may be used to bind to a receptor that is overly expressed in that lung cancer such as a folate receptor. Targeting also can be achieved by causing the hydrogel particle to change chemical bonding or conformation when the particle is in a microenvironment that is unique to the disease site, such as in infection in the lung where inflammatory response of the lungs to the microorganisms causes higher concentrations of chemicals and mediators that can cause the hydrogel to actively change its nature. This could be to cause pH sensitive changes in the hydrogel network so that the drug loaded in the hydrogel particle is rapidly released when pH decreases so as to concentrate the drug release to areas where the disease is most pronounced.

Example 1

Synthesis of PEG Hydrogel

An eight-arm, hydroxyterminated PEGs with total number average molecular weights (Mw) of approximately 10 and 20 kD are acrylated to a degree of functionalization exceeding 95% after azeotropic distillation followed by reaction with acryloyl chloride in the presence of triethylamine as has previously been described by Elbert, D. L., et al., Self-selective Reactions in the Design of Materials for Controlled Delivery of Proteins. Journal of Controlled Release, 2001. 76: p. 11-25. Hydrogels are formed by mixing the chosen PEG-acrylate with either dithiothreitol or PEG-dithiol, Mw 3.1 kD at a 1:1 stoichiometric ratio of acrylates to thiols in 50 mM phosphate buffered solution (PBS, pH 7.8). Each reactant is dissolved separately in an aliquot of PBS. The amount of PBS is varied to give the desired total precursor concentration (wt %) upon mixing. The two solutions are mixed vigorously in 1.5 mL plastic tubes and centrifuged to remove bubbles. The sealed tube containing the mixture is placed at 37° C., and allowed to react overnight to ensure complete conversion.

There are significant toxicological and compatibility advantages of using such a reaction to form gels under physiological conditions for drug delivery applications Peppas, N. A., et al., Physicochemical foundations and structural design of hydrogelst in medicine and biology. Annu. Rev. Biomed. Eng., 2000. 2: p. 9-29. The degradation rate of the polymer is determined by various factors including the initial water content of the hydrogel network. This is initial water content is controlled by the crosslinker and the molecular weight of the PEG acrylate. Drug release from the hydrogel is determined by the relative sizes of the drug molecule and the mesh size of the crosslinked network. If drug size is assumed constant (though drug suspension particles could conceivably be modulated in some cases), drug release can be modulated by decreasing the mesh size. This is achieved by decreasing the length of the polymers (molecular weight).

Poly(acrylic acid-co-acrylamide) hydrogels were synthesized using similar methods to those described by Chen, J. et al. "Synthesis and characterization of superporous hydrogel composites", Journal of Controlled Release 65: pp. 73-82 (1999), the teachings of which are incorporated herein by reference.

Alternatively, the swelling particles for pulmonary drug delivery may be formed from polymers or blends of polymers with different polyester/amino acid backbones and grafted amino acid side chains, For example, poly(lactic acid-co-lysine-graft-alanine-lysine) (PLAL-Ala-Lys), or a blend of PLAL-Lys with poly(lactic acid-co-glycolic acid-block-ethylene oxide) (PLGA-PEG) (PLAL-Lys-PLGA-PEG) may be used.

In the synthesis, the graft copolymers may be tailored to optimize different characteristics of the swelling particle including: i) interactions between the agent to be delivered and the copolymer to provide stabilization of the agent and retention of activity upon delivery; ii) rate of polymer degradation and, thereby, rate of drug release profiles; iii) surface characteristics and targeting capabilities via chemical modification; and iv) particle porosity.

Example 2

Dual Action Mucolytic-Therapeutic Drug Delivery Vector for Cystic Fibrosis

From the moment an aerosolized drug is expelled from the metered-dose inhaler or nebulizer and enters the mouth, through its journey past the pharynx, down the trachea and bronchioles into the deeper recesses of the airways toward its site of action, and finally to its degradation and removal, aerosolized agents are under the influence of a multitude of factors, which may be grouped into two general categories. Those determinants which govern the deposition of the aerosolized agent onto the airway lumen surface are termed physical properties, and include a particle's diameter and density. The properties that determine the fate of the drug subsequent to its impaction on the luminal surface, including its absorption, metabolism and excretion, are referred to pharmacokinetic factors.

Accordingly, the physical and pharmacokinetic factors of an aerosolized particle must be precisely tailored to complement one another as a means of delivering the most effective dosage possible while simultaneously minimizing drug waste and circumventing undesired collateral reactions.

With these considerations in mind, this EXAMPLE pursuant to another illustrative embodiment provide a novel dual action mucolytic-therapeutic hydrogel drug delivery vector for the treatment of cystic fibrosis as a means of significantly improving the efficacy of current FDA approved cystic fibrosis therapeutics. Furthermore, although this delivery system was initially designed specifically for cystic fibrosis, it can also serve as a therapeutic delivery vector for other pulmonary disorders, including lung cancer, COPD, and asthma.

Due to the large amounts of pathogens and debris that we inhale with each breath, the lung possesses multiple lines of defense to prevent infection and maintain homeostasis. From the trachea to the terminal bronchioles, an area collectively referred to as the central airways, the surface of the luminal epithelium is coated with a film of fluid that is composed of a sol and gel phase and referred to respectively as the periciliary and mucus layers. Each of these two layers play an important role in keeping the lung clear of pathogens, and their precise composition is essential to the effective clearance of foreign particles from the airways. The overlying thick and viscous mucus acts as a barrier to prevent the passage of inhaled pathogens and other foreign debris to the underlying epithelial cells below. The periciliary fluid, while not a direct obstacle in the manner of the superjacent mucus layer, is no less important to ensuring the lung is kept clean of pathogens. Through the rhythmic and concerted beating of the epithelial cilia within the periciliary fluid, mucus is propelled in the cephalic direction towards the pharynx and removed from the airway via expectoration or ingestion into the gastrointestinal tract, a process referred to as the mucociliary escalator. Therefore, any aerosolized agent remaining trapped within the mucus layer is carried along and summarily removed from the respiratory tract.

The periciliary fluid is maintained at an optimal volume which ensures that only the tips of the cilia contact the overlying mucus, propelling it onward. The volume and ionic composition of the periciliary fluid layer is the end result of the delicate balance between absorption and secretion of $H_2O$ and ions (specifically $Na^+$ and $Cl^-$). This balance is tightly regulated through the concerted action of ion channels located in the apical surface of pulmonary epithelial cells. Absorption of fluid is controlled primarily by the activity of the amiloride-sensitive epithelial Na channel (ENAC). The absorption of osmotically active $Na^+$ ions from the periciliary fluid into the epithelial cells drives water from apical to the basolateral surface of the cell, decreasing the volume of the periciliary fluid. This action is countered by both the outward rectifying chloride channel (ORCC) and the cystic fibrosis transmembrane conductance regulator (CFTR) channel, which allows the passage of chloride ions out of the cell and into the lumen, carrying water along and restoring the volume of the periciliary fluid.

In cystic fibrosis (CF), the most prevalent autosomal recessive genetic disorder in Caucasians, the gene encoding the CFTR channel contains a mutation which results in the translation of a defective protein. The majority of the mutated CFTR protein is degraded in the endoplasmic reticulum by the 26S proteosome, and the small amount that does reach the plasma membrane of the apical surface does not function properly and no longer allows the passage of chloride ions into the pulmonary lumen. This decreased transport of chloride ions results in a reduced amount of water entering the periciliary fluid, and since the $Na^+$ channels are still absorbing water at a normal rate, the volume of the periciliary fluid is considerably reduced. The upper region of the cilia become embedded in the mucous layer, significantly hindering their movement and leading to the cessation of the mucociliary escalator. The mucus layer becomes increasingly viscous and stagnant, allowing bacteria colonies to rapidly accumulate throughout the lung. This increased infestation produces a vigorous response from the immune cells of the body, which over time significantly deteriorates the lung, and eventually results in death.

The ideal solution would be to administer gene therapy that would replace the defective copy in the chromosome with one that encodes for a functioning CFTR channel. Unfortunately, while this is a very active area of research, due to numerous setbacks gene therapy is still not a viable option, and treatment of the physical manifestations of the genetic disorder remains the only route to treat CF. The current therapy consists primarily of the mucolytic N-acetylcysteine, which severs the bonds between adjacent mucin glycoproteins and reduces the viscosity of the mucus, and administration of various antibiotics targeting the numerous bacterial colonies infesting the lungs of CF patients. These treatments are administered in aerosolized form and may be prescribed either separate or in tandem. While this therapy does help alleviate some of the complications of CF, it is an extremely wasteful procedure and much can be done to improve its efficacy while simultaneously reducing its cost in both time and money. For instance, the antibiotic will only be effective against the bacteria that it encounters as soon as it is deposited in the airways. Once the therapeutic contacts the viscous mucus it will be become entrapped, completely abrogating its bactericidal activity. Conversely, no matter where the mucolytic lands it will be able to decrease the viscosity of the stagnant mucus in its vicinity. However, the mucolytic alone does nothing to combat the numerous bacterial colonies populating the airways, and which are the direct source of the complications of CF.

This EXAMPLE provides swellable particles for delivering both the mucolytic and therapeutic simultaneously within the same aerosol dose. In this manner the mucolytic will reduce the viscosity of the mucus and increase the radius of diffusion of the therapeutic, bringing it into contact with a greater number of bacteria and significantly improving its effectiveness. The use of swellable particles to this end takes into consideration that any therapy administered this way, where the therapeutic and mucolytic are delivered in their free (i.e. unencapsulated) form, will be short-lived. The immediate impact of the therapy will permit the cilia to beat with increased frequency and improve the function of the mucociliary escalator, which in turn will remove much of the mucus and bacteria, accompanied by the therapeutics, from the lung. However, as this treatment does nothing to address the underlying genetic defect, the mucus will once again become stagnant and viscous, allowing the remaining bacteria an opportunity to divide and multiply, so that soon after administration the condition in the lung is returned to its pre-therapy state. On average, cystic fibrosis patients must spend approximately three hours per day self-medicating. Not only does this strict and inflexible routine have a tremendous impact on their quality of life, it also gives rise to patient non-compliance with their prescribed therapy. Due to the rigorous nature of their treatment, a patient may either accidentally or intentionally forgo a day or two of therapy, believing that such a brief absence of medication will not be severely detrimental to their health. However, when fighting against bacteria which require only hours to replicate this negligence may yield severe consequences. How then does one solve this paradox of alleviating the stringency of the therapy as a means of improving patient compliance while simultaneously ensuring the delivery of the prescribed dose of medication? The solution to this question is found in sustained release therapy, where the therapeutics are released continuously over a period of days, if not weeks, allowing the patient to receive their prescribed dosage while increasing the interval between administration.

The use of swellable particles to this end takes into consideration the problem that delivery via aerosolized particles completely ignores the aerodynamics which governs the deposition of aerosolized particles in the lung. In aerosols a very important property is the aerodynamic diameter ($d_a$) of a particle. The aerodynamic diameter is a method used to standardize the aerodynamical properties of particles regardless of shape, density, size, or actual diameter, and may be thought of as the diameter of a water droplet having the same aerodynamic properties as described above. The most significant information derived from the aerodynamic diameter is that a particle with a given aerodynamic diameter will be aerodynamically indistinguishable from other particles of different size, shape, diameter or density having the same aerodynamic diameter.

As the preceding paragraph demonstrates, the aerodynamic properties of an aerosolized particle are heavily dependant upon both its' diameter and density, and the slightest alteration of either property will result in the deposition of the particle in a different region of the lung. Therefore, attempting to deliver a mixture of mucolytic and therapeutic either in their free form or encapsulated within discreet delivery vectors will result in non-uniform deposition, since the two do not have identical diameters and densities and therefore will not possess identical aerodynamic properties. Consequently, the EXAMPLE provides for delivery of both the mucolytic agent and therapeutic agent together using the swellable particles.

Moreover, the swellable particles provide a preferred CF therapeutic vector to provide sustained release of the therapeutic agent and also capability to carry both mucolytic and therapeutic agents. Furthermore, when designing a delivery vector for human consumption, it is essential that it is biocompatible, non-toxic, and non-immunogenic. The hydrogel particles described above encapsulating the therapeutic and mucolytic agents within a crosslinked, hydrophilic polymer network achieves the sustained release of the agents. For example, when a hydrogel is placed in an aqueous environment it readily imbibes water and swells, stretching its polymer chains and producing numerous pores that will permit the drugs within to diffuse out. Hydrogels are especially relevant for drug delivery in the lung, as the initial surface that a delivery vector encounters is the viscous mucus, which is primarily composed of hydrophilic mucin glycoproteins, which readily attract water. Therefore, hydrophilic polymer hydrogels are ideally suited to siphon water away from the mucus, allowing the hydrogel to swell and release its therapeutic cargo.

The most important factor when developing a hydrogel network is the selection of a suitable hydrophilic polymer, and due its numerous beneficial properties, polyethylene glycol (PEG) is described above. Among the attributes that make this FDA approved polymer attractive include that it is non-toxic, biocompatible, non-immunogenic and strongly hydrophilic, allowing it to draw water away from the mucus to promote hydrogel swelling. Furthermore, PEG exhibits almost no protein adsorption, allowing it to elude the ubiquitous macrophages patrolling the labyrinth of the pulmonary passages. These characteristics combine to make PEG the most promising candidate for employment in pulmonary drug delivery.

The antibiotics used to treat CF include tobramycin and gentamycin, which are large, bulky, hydrophobic macromolecules. While their hydrophobic nature prevents the antibiotics from being incorporated in their free form, it permits them to be readily encapsulated within the core of a liposome nanoparticle. The liposome nanoparticle in turn possesses a hydrophilic surface, allowing it be easily incorporated inside the hydrogel matrix. Furthermore, by adjusting the size of both the liposome nanoparticle and the pores of the polymer matrix, the release rate of the antibiotic from the hydrogel may be accurately controlled.

The next step is to encapsulate the mucolytic (e.g. N-acetylcysteine designated NACS) within the hydrogel. Due to the small size of NACS and its hydrophilic nature, if it is simply loaded into the hydrogel in its free state, the moment the hydrogel begins to swell NACS will be released from the lung in an undesirable single, rapid burst. To overcome this, the NACS is covalently bonded to the PEG polymer network, while still retaining its mucolytic activity. The advantage of this method is that as the hydrolytically labile ester bonds are broken NACS will be released into the environment. This ensures that mucolytic will be released throughout the entire lifetime of the hydrogel, providing the sought after sustained release to accompany the diffusion of the antibiotic from the gel.

As previously mentioned, NACS is extremely soluble in water (100 mg/mL), thus precluding its incorporation into nanoparticles similar to those encapsulating the hydrophobic antibiotic.

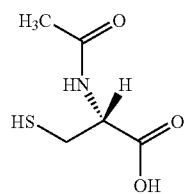

The structure of N-acetylcysteine (pictured above) affords us two functional groups with which to create a hydrolytically labile bond to attach the mucolytic agent to the PEG-polymer network. The release rate of the therapeutic will depend on both the kinetics of the cleavage/degradation of the drug-network linkage (which is described by an appropriate rate constant), and upon the diffusion rate of the free molecule from the matrix of the polymer network. The crosslinker employed in our hydrogels is dithiothreitol, which contains two thiol moieties that readily react with our functionalized PEG octa-acrylates without the need of organic solvents at body temperature and biological pH.

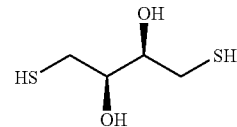

However, since NACS contains only one thiol, it could either form a disulfide bond with another NACS molecule, or it may react with the acrylate group of the polymer. Either way, its function as a mucolytic agent would be significantly disrupted, if not abrogated entirely.

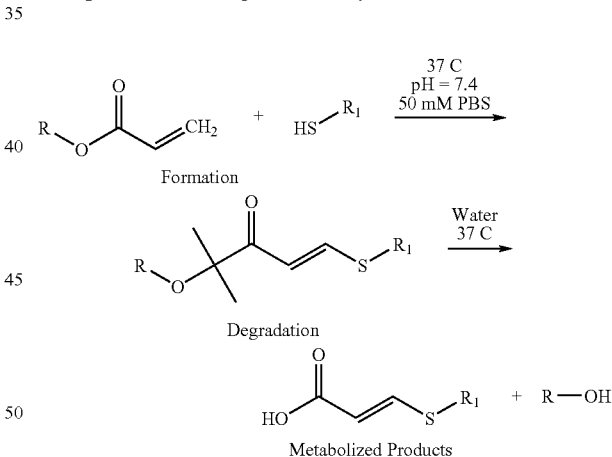

As shown in the reaction scheme (which is only showing the acrylate end group of the 8-arm PEG-acrylate coupling with the thiol functionalized end of DTT), the initial step is the Michael addition of the thiol to the acrylate group. Following this reaction, the next step is an ester hydrolysis in which an alcohol and a carboxylic acid are formed (the exact opposite of the Fisher esterification reaction). But as can be seen, the sulfur atoms (since what is formed is actually a dicarboxylic acid, since dithiothreitol contains two S—H groups per molecule) are no longer in their reduced thiol forms. Instead, as shown below, they are bonded to two carbon atoms, forming C—S—C linkages, and no longer able to participate in disulfide bonding with the thiol moieties of the mucin polymers.

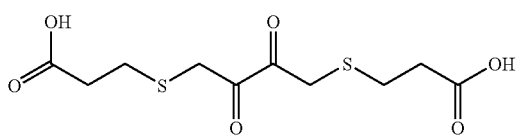

Therefore, control of the release of NACS can be achieved by reacting dithiothreitol with N-acetylcysteine, in perhaps a molar ratio of at least 4:1 (DTT:NACS), prior to the crosslinking reaction with the 8-arm PEG polymer. This will allow the thiols of DTT to react with the thiol of NACS. The advantage of NACS is that it is already an FDA approved drug, and similar to other thiol compounds, will react readily without the need for harmful solvents or reaction conditions. The structure of the cleaved molecule (following ester hydrolysis) is shown below:

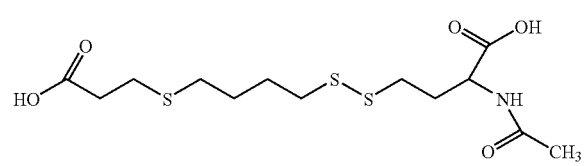

As opposed to the previous compound, this molecule contains a disulfide S—S linkage, which readily competes with mucin polymers for their disulfide bonds, since the only exchange that is occurring is one disulfide bond for another (requiring no significant cost in energy, unlike an exchange from a low-energy bond to a high-energy bond, which would be thermodynamically unfavorable and would possess a large transition barrier) this exchange of disulfide bonds occurs under very mild conditions (essentially mixing the chemicals in a PBS buffer).

Although there will certainly be some NACS-NACS disulfide bonding, this is not an irreversible linkage, and a greater amount of DTT will ensure that the majority of the NACS will be bound to the crosslinker (theoretically, every molecule of NACS will yield one S—S active mucolytic bond). By increasing the amount of DTT used we can ensure that the hydrogel has the majority of the crosslinkable moieties occupied, thus maintaining structural stability, while simultaneously possessing enough DTT-NACS to exhibit a significant enhancement in hydrogel permeability through the mucus. And while it is true that any DTT that is bound to NACS will not be able to form a crosslink with another PEG molecule, recent experiments show that firm hydrogels can be formed with at least 30% concentration of crosslinker compared to the polymer (that is to say that there are enough DTT molecules to theoretically occupy 30% of the PEG acrylate groups).

Synthesis of Biocompatible Hydrogels from 8-Arm Peg Acrylate Containing Rhodamine and N-acetylcysteine The initial synthesis of the acrylated 8-arm PEG (Mw=10 kDa and 20 kDa) was based upon the work of Hubbell et al. *Journal of Controlled Release* 76:11-25 (2001) as described above. For example, ten (10) g of 8-arm PEG (20 kDa, Nektar) was dissolved in 200 mL of toluene and distilled azeotropically for 2 hrs. The resulting solution was then allowed to cool to 50 C under argon. Two (2) mL of triethylamine was added to 50 mL of dichloromethane which was then added to the reaction solution. An amount (1.3 mL) of acryloyl chloride was then added dropwise and the reaction proceeded under argon in the dark for 20 hrs. The resulting opaque pale yellow solution was then filtered multiple times until clear. Anhydrous sodium carbonate was added to the solution and stirred for two hours to remove any water that was present. The solution was filtered to remove the sodium carbonate and was then evaporated under reduced pressure. Diethylether was then added to the solution and the reaction flask was placed in an ice bath to allow the product (acrylated PEG) to precipitate. The product was collected by filtration and repeatedly washed with diethylether. The average yield was around 85%.

Firm and stable PEG hydrogels can be formed with an acrylate:thiol stoichiometric ratio >1 and with a thiol amount as low as 60% (0.60 ratio of thiol/acrylate) of the amount of acrylate moieties present. Generally, dithiothreitol, having two thiols per molecule, forms crosslinks between polymer molecules to form the hydrogel network. To form hydrogels with N-acetylcysteine mucolytic agent covalently bound to the hydrogel network, we reacted 5 mg of dithiothreitol with 1.1 mg of N-acetylcysteine, each dissolved in 20 ul of 1×PBS (7.4 pH). N-acetylcysteine has the capacity to form a bond between it's thiol group and either the acrylated polymer or to dithiothreitol via S—S disulfide bonds formed from two thiol groups. Stoichiometrically, at the above mentioned concentrations of reactants, if all of the thiol groups on the N-acetylcysteine are each bound to one unique dithiothreitol molecule, there will still remain enough free thiol groups on dithiothreitol molecules to form sufficient crosslinking between the polymermolecules such that stable hydrogels are formed. This solution was added to 0.160 g of acrylated 8-arm PEG (20 kDa) dissolved in 200 μl of 1×PBS (pH 7.4). To this solution was added 10 μl of Rhodamine therapeutic agent (40 mg/mL 1×PBS (pH 7.4)). Seventy (70) μl aliquots of the solution was placed between microscope slides coated with SigmaCote (Sigma Chemical Co.), and separated by 1 mm spacers. The gels were allowed to cure for 24 hours in a humid environment at 37 C. The cured gels were milled after drying, in a micro-ball mill (from Dentsply Rinn, Elgin, Ill.) cooled using liquid nitrogen, to produce swellable particles having volume mean diameters of between 1.1 and 3 μm and a span of 2.2 (span=(D90–D10)/D50) where D50 is median diameter and D10 and D90 are respective $10^{th}$ and $90^{th}$ percentile diameters (e.g. for D10, 10% of particles are less than this diameter).

As discussed above, in this EXAMPLE, dual delivery of both mucolytic and therapeutic agents would serve to significantly enhance the effectiveness of the present CF therapy by increasing the radius of diffusion of the therapeutic, allowing it to contact a larger number of bacteria, while simultaneously improving the function of the mucociliary escalator. However, this dual-action aerosolized hydrogel is not limited for use to cystic fibrosis therapy. As previously mentioned, during physiological conditions the lumen of the pulmonary passages are coated with a layer of mucus serving as a barrier to inhaled particles. This mucus is continuously removed via the mucociliary escalator, requiring approximately 10 hours to eject inhaled debris from the furthest reaches of the lung, and much less time to clear the upper passages where the majority of malignant tumors dwell. Incapable of distinguishing between therapeutic aerosols and pathogens, the mucociliary escalator expels friend and foe alike with equal vigor. Accordingly, any inhaled therapeutic has only a brief window in which to penetrate the mucous barrier, attain the underlying epithelium, and deliver its medicinal cargo, else it forever loses any opportunity for efficacy. Furthermore, when one also considers that the tumor is not uniformly distributed throughout the lung and that there is only a specific region where the therapeutic will be effective, the aforementioned brief window of action is further narrowed. By controlling the aerodynamic properties of a particle via its diameter and density, an aerosol can be tailored so that the majority of the particles will arrive at the desired location in the lung. However, once the particle lands on the surface of the lumen, the onus is entirely upon the particle to penetrate the mucus prior to its expulsion from the lung.

Therefore, it becomes evident that the quicker a particle can pass through the viscous mucus, the greater its chances to provide a beneficial effect. By combining a mucolytic with a cytotoxic agent, corticosteroid or bronchodilator for the treatment of lung cancer, COPD, and asthma respectively, the efficacy of the treatments will be increased and the amount of drug wasted via the action of the mucociliary escalator will be markedly reduced.

Targeting molecules can be attached to the swelling particles via reactive functional groups on the particles. For example, targeting molecules can be attached to the amino acid groups of functionalized polyester graft copolymer particles, such as PLAL-Lys particles. Targeting molecules permit binding interaction of the particle with specific receptor sites, such as those within the lungs. The particles can be targeted by attachment of ligands which specifically or non-specifically bind to particular targets. Exemplary targeting molecules include antibodies and fragments thereof including the variable regions, lectins, and hormones or other organic molecules capable of specific binding for example to receptors on the surfaces of the target cells.

Although the invention has been described above with respect to certain illustrative embodiments, those skilled in the art will appreciate that changes, modifications and the like can be made thereto without departing from the spirit and scope of the invention as defined in the appended claims.

What is claimed is:

1. A method of delivering a working agent to the pulmonary system, comprising:
   providing particles comprising a biodegradable material and having a mass median aerodynamic diameter not exceeding 5 µm, said particles being swellable by hydration to a larger particle size that is greater than 6 µm volume mean diameter;
   providing the working agent on or in the particles;
   forming the swellable particles to have a polymer network and chemically bonding the working agent to the polymer network; and
   delivering the particles to the pulmonary system where the particles reside in airways and swell to the larger size that is greater than 6 µm volume mean diameter.

2. The method of claim 1 wherein the particles are sized and configured to reside in airways of the respiratory tract.

3. The method of claim 2 wherein the particles are sized and configured to reside in alveolar regions of the lung.

4. The method of claim 1 wherein the delivering step comprises delivering the particles from an inhaler.

5. The method of claim 1 wherein the delivering step comprises delivering the particles by dry powder insufflation.

6. The method of claim 1 wherein the delivering step comprises delivering the particles by liquid spray or nebulizing.

7. The method of claim 1 wherein the working agent is delivered to treat cystic fibrosis, lung cancer, asthma, chronic obstructive pulmonary disease, acute bronchitis, or emphysema.

8. The method of claim 1 wherein the working agent comprises one or more of a therapeutic agent, a diagnostic agent, a prophylactic agent, or an imaging agent.

9. The method of claim 8 wherein the working agent comprises a mucolytic agent.

10. The method of claim 9 wherein the working agent also comprises an antibiotic agent.

11. The method of claim 9 wherein the working agent also comprises a cytotoxic agent.

12. The method of claim 9 wherein the working agent also comprises an RNA interfering agent.

13. The method of claim 9 wherein the working agent also comprises a gene.

14. The method of claim 8 wherein the working agent comprises multiple cytotoxic agents.

15. The method of claim 8 wherein the working agent comprises a cytotoxic agent and RNA interfering agent.

16. A method of delivering a working agent to the pulmonary system, the method comprising:
   providing particles comprising a biodegradable material and having a mass median aerodynamic diameter not exceeding 5 µm, said particles being swellable by hydration to a larger particle size that is greater than 6 µm volume mean diameter;
   entrapping the working agent in nanoparticles and then incorporating the nanoparticles on or in the swellable particles; and
   delivering the particles to the pulmonary system where the particles reside in airways and swell to the larger size that is greater than 6 µm volume mean diameter.

17. A method of delivering a working agent to the pulmonary system, comprising:
   forming particles having a desired polymer network, the particles comprising a biodegradable material and having a mass median aerodynamic diameter not exceeding 5 µm, said particles being swellable by hydration to a larger particle size that is greater than 6 µm volume mean diameter;
   binding a working agent and a mucolytic agent with the polymer network so as to facilitate prolonged and localized release of the mucolytic agent upon delivery to the pulmonary system and thereby increase diffusion and efficacy of at least one of the working agent and the particle; and
   delivering the particles to the pulmonary system where the particles are sized and configured to reside in airways and swell to the larger size that is greater than 6 µm volume mean diameter.

18. The method of claim 17, wherein the forming step comprises combining a polymer with a crosslinker.

* * * * *